United States Patent
Giannozzi et al.

(10) Patent No.: US 9,655,508 B2
(45) Date of Patent: May 23, 2017

(54) LED LIGHT PLACIDO DISC PROJECTOR FOR A CORNEAL TOPOGRAPHY SYSTEM

(71) Applicant: Costruzioni Strumenti Oftalmici C.S.O. S.r.L., Scandicci (Florence) (IT)

(72) Inventors: Franco Giannozzi, Scandicci (IT); Simone Spadini, Florence (IT)

(73) Assignee: COSTRUZIONI STRUMENTI OFTALMICI C.S.O. S.R.L., Scandicci (Florence) (IT)

( * ) Notice: Subject to any disclaimer, the term of this patent is extended or adjusted under 35 U.S.C. 154(b) by 29 days.

(21) Appl. No.: 14/647,575

(22) PCT Filed: Nov. 26, 2013

(86) PCT No.: PCT/IB2013/060406
§ 371 (c)(1),
(2) Date: May 27, 2015

(87) PCT Pub. No.: WO2014/083498
PCT Pub. Date: Jun. 5, 2014

(65) Prior Publication Data
US 2015/0289758 A1     Oct. 15, 2015

(30) Foreign Application Priority Data

Nov. 28, 2012  (IT) .............. F12012A0262

(51) Int. Cl.
    *A61B 3/10*    (2006.01)
    *A61B 3/00*    (2006.01)
    *A61B 3/107*   (2006.01)

(52) U.S. Cl.
    CPC ............ *A61B 3/0008* (2013.01); *A61B 3/107* (2013.01)

(58) Field of Classification Search
    CPC ..................... A61B 3/107; A61B 3/0008
    USPC ....................................... 351/212
    See application file for complete search history.

(56) References Cited

U.S. PATENT DOCUMENTS 5,500,697 A    3/1996    Fujieda

FOREIGN PATENT DOCUMENTS

JP    2006158749    6/2006
WO    2011/148349   12/2011

OTHER PUBLICATIONS

International Search Report issued in PCT Application No. PCT/IB2013/060406.

*Primary Examiner* — Mahidere Sahle
(74) *Attorney, Agent, or Firm* — Lucas & Mercanti, LLP

(57) ABSTRACT

The present invention generally refers to corneal topography systems. More specifically, it regards a Placido disc projector (or simply Placido disc) for a corneal topography system, having a novel arrangement of LED lighting.

24 Claims, 2 Drawing Sheets

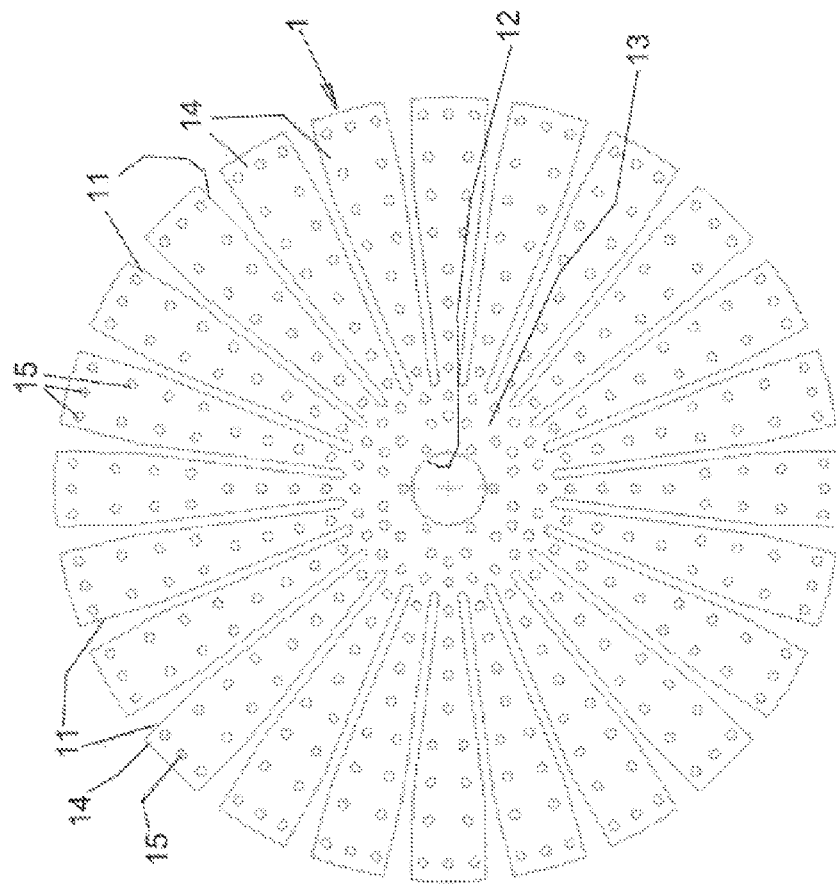
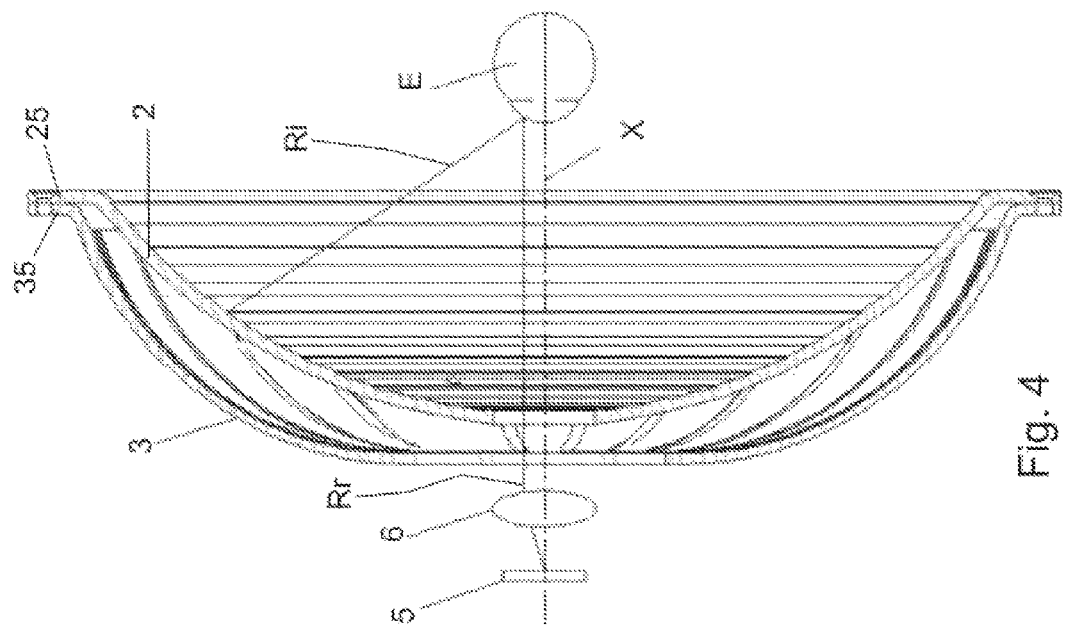

LED LIGHT PLACIDO DISC PROJECTOR FOR A CORNEAL TOPOGRAPHY SYSTEM

CROSS-REFERENCE TO RELATED APPLICATIONS

This application is a 371 of PCT/IB2013/060406, filed Nov. 26, 2013, which claims the benefit of Italian Patent Application No. FI2012A000262, filed Nov. 28, 2012.

DESCRIPTION

Field of the Invention

The present invention generally refers to corneal topography systems. More specifically, it regards a Placido disc projector (or simply Placido disc) for a corneal topography system, having a novel arrangement of LED lighting.

Background of the Invention

It is well known for a long time the corneal topography system making use of the analysis of an image reflected by the cornea. The reflection, called "Purkinje image", is generated by means of luminous patterns placed at the front of an eye under examination.

Among the patterns used for studying the corneal surface, the most widespread, for its being capable of showing at best the deformations and the curvature variations, is the one generated by the Placido disc projector.

A Placido disc projector consists traditionally of disc shaped body, indeed having the shape of a truncated cone or a paraboloid, made of a translucent material, on which there are arranged (thorough dyeing or applied in any other manner) concentric black (or in any case opaque) rings, suitably spaced. In this way a light source arranged at the rear of the body, i.e. at the convex side, is capable of projecting onto the eye of a patient placed at the concave side, and namely onto the cornea, a Placido image or pattern comprising indeed a number of concentric light rings.

As a light source for lighting the body at/from the rear, various solutions have been experienced in the known art. Among them there is the use of a toroid-shaped neon lamp (so-called fluorescent ring light) arranged coaxially with the disc (obviously at its rear side). Another known solutions provides for exploiting the light reflection through the thickness of the disc, or in a gap defined inside the same, in this latter case the disc comprising two bodies (both having the shape of a paraboloid, a truncated cone etc.) mutually associated and spaced. According to this solution the lighting elements are arranged at the periphery of the disc. A further known technique provides for the use of an electroluminescent substrate integrated with the disc body.

Such system can attain the result of a uniform and suitably intense lighting of the disc. However, such achievement is not a sufficient condition in order to obtain an optimal result of the topographic examination.

Indeed, even when the disc is uniformly lit, the projection of the pattern onto the cornea and its capture by an optical system and relative image-capturing sensor, will not result homogeneous due to the curvature of the cornea and the angle of the take/capture. The incidence of the light on the spherical surface of the cornea has actually a different behavior at the different points and thus generates a reflection that is more or less bright. The processing of the image captured by the sensor is carried out by a software that analyses the various grey levels, and therefore it can be easily understood that it is not only and not much the homogeneity of the lighting as such, but rather the homogeneity of the captured image that represents a fundamental requirement for a high quality result of the topographic analysis.

SUMMARY OF THE INVENTION

The applicant has now developed a solution that permits to reach the above mentioned object, that is to obtain an image reflected by the cornea (Purkinje image) following to a projection carried out by a generally disc-shaped lighting body, typically a paraboloid, that has qualities of uniformity presently unattained by any known illumination system.

According to the invention, such a solution is represented by a Placido disc projector with a LED lighting having the essential characteristics defined by the first of the appended claims. A method for manufacturing the projector follows essentially the steps indicated in the enclosed claim 13.

BRIEF DESCRIPTION OF THE DRAWINGS

The features and advantages of the Placido disc projector with a LED lighting according to the present invention will be apparent from the following description of an embodiment thereof, given as an example and not limitative, with reference to the attached drawings in which:

FIG. 1 shows in a flat blank development a printed circuit board that according to the invention is to be associated to disc-shaped body made of a translucent material and bearing a Placido pattern with black concentric rings;

FIG. 4 shows the projector according to the invention, represented schematically and out of scale, there being in particular magnified the distance between the body and the support, the projector being sectioned diametrically and represented in the context of a corneal topography system.

DETAILED DESCRIPTION OF THE INVENTION

Figure 3:
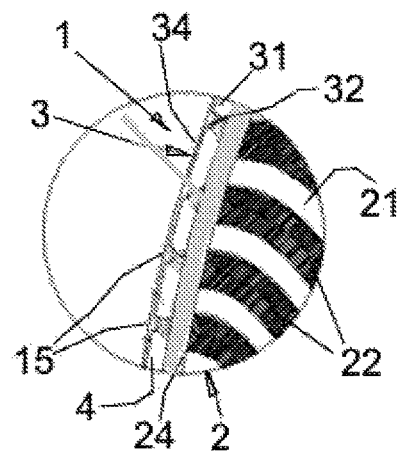
FIG. 3 is an enlarged view of the area enclosed by the circle III in FIG. 2, the board being in this case shown in complete adhesion to the support.

Referring to the above figures, and in particular for the time being to FIG. 1, according to the invention there is provided to form a thin and foldable/pliable printed circuit board, by making use e.g. of a material such as the so-called FR-4 (composite material comprising a fiberglass cloth combined with an epoxy resin), as a support and insulation sheet for the copper conductive tracks. The pliability or flexibility of the electronic board 1, given the nature of the material used as a support, is a consequence of the reduced width with which it is manufactured, in the range of a few tenths of mm, e.g. 0.3 mm, obtainable with technologies that are available to the skilled person, providing for instance the superimposition of various thin layers of copper and insulating material, the choice, of the number of layers permitting to attain different properties in terms of performance and pliability.

The printed circuit board 1, seen in a flat development as indeed in FIG. 1, is in the example a blank with a generally circular peripheral outline, with a crown of deep radial cuts 11 that extend starting from the peripheral edge and reaching a point nearby the center, where a hole 12 is formed. The hole is thus surrounded by a ring-shaped portion 13 of the board, from which strips 14 extend, the strips being mutually spaced by respective cuts 11. Other and different distributions of cuts can be provided, achieving the same result (clarified in the following part of the description) of making the board generally deformable.

The circumference of the board 1 is set as a function of the size of a paraboloid disc shaped body with a Placido pattern to which the same board is to be associated, as explained hereafter. The board 1 includes a plurality of LEDs 15 that are distributed also on the ring portion 13 and on the strips 14 in spaced annular arrays. Also the distribution of the arrays of LEDs 15 is set in accordance with the rigid body bearing the Placido pattern, the number and distance of the annular arrays being correspondent to the number and distance among the black rings of the pattern. The LEDs here employed are diffused light SMD micro-LEDs with a wide viewing angle, possibly greater than 130°. As a mere example, a LED type that can be employed is the one marketed by the company Osram® with the code LT Q39G-Q1S2-25-1 (wavelength 530 nm, luminous intensity 280 mcd, viewing angle 155°).

In each array the LEDs 15 are arranged with a high linear density (about 15 mm as an average distance among consecutive LEDs in the same range) for a total of about 350 LEDs in a disc shaped body having the standard size that is usual in the field. Moreover, the circuit is designed so as to make single LEDs, or groups of LEDs in a circular sector, or else the ranges of groups of adjacent arrays, controllable in a mutually independent manner. In this way, the lighting in the various area can be varied and optimize, even with a fine tuning LED by LED, according to the needs.

As mentioned, the board 1 has to be associated with the body bearing the typical ring pattern of a Placido disc projector. In a preferred embodiment of the invention, given a paraboloid body 2 in the usual translucent material, preferably opal glass or in any case with a high diffusion capacity, bearing at the concave side 21 the usual as well pattern with black concentric rings 22, and at the center an opening 23 for the capture of the reflected image, the board 1 is arranged at a certain distance from the same body 2, on a support 3 that in its turn has the shape of a paraboloid, with a curvature that corresponds with the curvature of the body 2, and that is connected at the rear of the body forming therewith a narrow gap 4. The mechanical connection between the body 2 and the support 3 can be typically realized with screw means that tighten respective peripheral flanges 25, 35, extending on a plane orthogonal with the common central axis of the body and the support.

Figure 2:
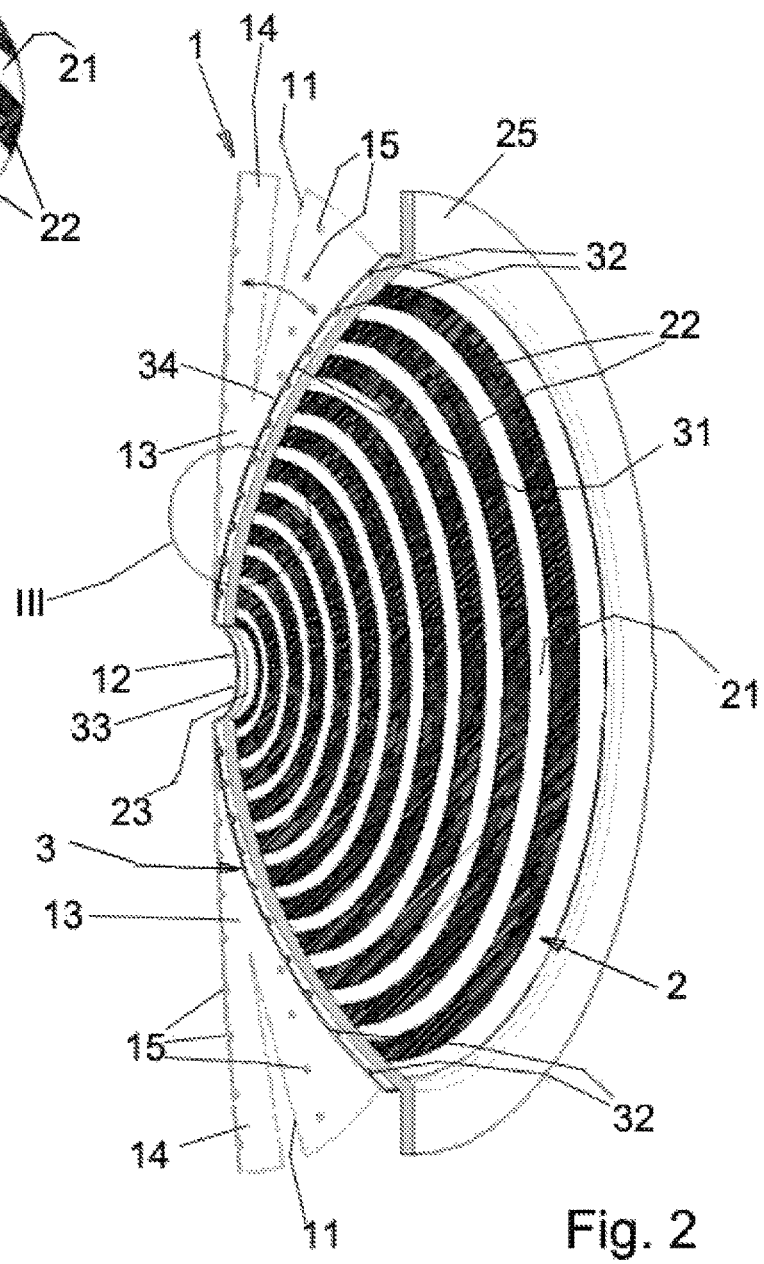
FIG. 2 is an axonometric view of a projector made with the circuit board of FIG. 1, the disc-shaped body and a support for the board being broken along a diametrical plane, the support being moreover incomplete, and the board partially detached, for the sake of illustrative clarity.

In the variant embodiment that is specifically represented in FIGS. 2 and 3, the board 1 is applied to a rear convex face 34 of the support 3. The support, besides to a central passage 33, provides for a distributions of through orifices 32 for the housing and fitting engagement of respective LEDs 15, so that the luminous radiation emitted by the LEDs can be directed towards the gap 4 and then the body 2. The application of the board on the support is typically carried out thanks to an adhesive substance, e.g. of a silicone type, and can even be carried out directly on the front concave side 31 of the support 3. In this latter case, the orifices 32 are no longer necessary. More generally speaking, other different constructions can be chosen to associate the board to the body 2, always according to the principle that the shape of the body must be followed in close proximity by the board. One of these construction can for instance make use of a board that, thanks to selected properties of shape, rigidity and arrangement of the cuts, once folded in a concave shape, can be self-supporting in such a conformation, and be connected to the body without requiring an additional and external support.

However, returning to the example here depicted, the board 1 becomes in practice a lining, even though with a certain spacing, of the convex side 24 of the disc body 2, following its shape and covering it completely. Thanks to the pliability of its material the board 1 can indeed be folded and shaped to match the convexity of the support 3, and then of the body 2. Thanks to the radial cuts 11 no creases are formed, creating a smooth and continuous lining, with no cracks, while the hole 12 permits not to shut the central opening 23 of the body 2 and the opening 33 of the support 3. When applying the board, as mentioned, the arrays of LEDs will be made to carefully correspond with the black rings 22. In this way the translucent strips between the rings will be capable of projecting a uniform and diffused light. The luminous radiation indeed diffuses within the material of the body, hiding the actual light source and creating a perfect light uniformity in each single pattern.

As a further remark for the sake of clarity, with particular reference to FIG. 4, there are shown in this figure, although schematically, the components that complete the topography system making use of the projector and the relevant optical path. An eye E of the patient to be examined is arranged at the concave side of the projector, in centered position, and collects the illuminating radiation Ri. The relative reflection Rr is collected along an imaging central optical axis X, coincident with the axis of the projector, by a sensor 5 with suitable image capturing optics 6 arranged at the convex side. The sensor 5 then obviously transmits the acquired signals to processing means, not shown.

According to the invention, it is then possible to shape the circuit board with the lighting means in a convex arrangement, even close to a spherical one, that can be therefore fit as a perfect lining a paraboloid disc having the curvature currently in use in the corneal topography instruments.

Thanks to the micro-LEDs thus applied and distributed, the quality of the illumination attained according to the present invention is remarkably higher than the known systems, in terms of uniformity of the reflected image. This assists and makes more accurate the subsequent processing and consequently the diagnostic result is considerably improved. This solution permits to optimize the distance between the light source and the Placido pattern, always taking care that the LEDs are shielded by the black rings, so that the quality of the illumination is further improved. A further specific advantage derives from the possibility of controlling independently the single LEDs or single groups of LEDs, region-by-region, consequently optimizing the luminous emission, again with the aim of maximizing the quality of the image capture, despite the variations of the specific circumstances of each exam.

Despite reference has been made to LED lighting means as a preferred embodiment, other lighting sources, typically of the punctiform type, can be used, if they can be equivalently applied in the technical context of a flexible circuit board as the one here proposed according to the invention.

The present invention has been here described with reference to its possible exemplifying embodiments. It should be understood that there may be other embodiments, even applicable to different topographic patterns than that with concentric rings, within the same inventive concept, as defined by the scope of protection of the following claims.

The invention claimed is:

1. A projector for corneal topography configured to project an image on the cornea of an eye (E) of a patient to be examined, the projector comprising a disc-shaped body with a paraboloid, conical or the like configuration, made of a translucent material and having a front concave surface on which a black or generally opaque pattern is formed, said pattern having a correspondence with said image, and lighting means arranged at an opposite side of said body with respect to said front surface, said lighting means comprising a plurality of lighting elements arranged on a printed circuit board having a concave shape extending superficially so as to cover at least said pattern at a determined distance from said disc-shaped body, the lighting elements being distributed only in correspondence with said pattern so that the same pattern blocks the direct light radiation towards the cornea, wherein said board is made from a support sheet in a foldable material and is shaped through folding of a flat blank of said sheet.

2. The projector according to claim 1, wherein said flat blank has a generally circular shape with a central hole and a number of radial cuts defining a plurality of strips extending from a ring-shaped portion.

3. The projector according to claim 1, wherein said foldable material is a fiberglass cloth combined with an epoxy resin.

4. The projector according to claim 1, wherein said support sheet has a width of few tenths of mm, e.g. 0.3 mm.

5. The projector according to claim 1, wherein said lighting elements comprise a plurality of LEDs regularly and extensively distributed in correspondence with said pattern.

6. The projector according to claim 5, wherein said pattern comprises a plurality of concentric rings, said LED being arranged in annular arrays corresponding with respective rings.

7. The projector according to claim 6, wherein in each annular array said LEDs are placed at an average distance of about 15 mm between two consecutive LEDs of the same array.

8. The projector according to claim 1, wherein the distance between the board and the disc-shaped body is substantially constant.

9. The projector according to claim 1, wherein said board is wrapped over, and supported by, a support in turn configured as a paraboloid, a cone or the like which is associated at the back of the disc-shaped body forming a gap between the support and the body.

10. The projector according to claim 9, wherein said board is applied over a rear convex face of the support which provides for a distribution of through orifices for arrangement and engagement of respective LEDs.

11. The projector according to claim 1, wherein said board has a circuit configured to make single LEDs or groups thereof controllable in a mutually independent manner.

12. The projector according to claim 11, wherein said groups of LEDs belong to respective circular sectors of the board, to single annular arrays or to sets of adjacent arrays.

13. A method for manufacturing a projector for corneal topography configured to project an image on the cornea of an eye (E) of a patient to be examined, comprising the steps of: providing a disc-shaped body with a paraboloid, conical or the like configuration, made of a translucent material and having a front concave surface on which a black or generally opaque pattern is formed, said pattern being congruent with said image, and a convex rear side opposite with respect to said concave front surface; arranging a printed circuit board comprising a number of lighting elements supported by a flat blank sheet made of a foldable material, the lighting elements being arranged on the sheet in accordance with said pattern; shaping the circuit board with the lighting elements through folding, following said convex surface; and stably associating the circuit board to said body at the side of said convex surface so that the lighting elements are distributed only in correspondence with said pattern.

14. The method according to claim 13, wherein said flat blank is formed in a generally circular shape with a central hole and a number of radial cuts defining a plurality of strips extending from a ring-shaped portion.

15. The method according to claim 13, wherein said foldable material is a fiberglass cloth combined with an epoxy resin.

16. The method according to claim 13, wherein said support sheet has a width of few tenths of mm, e.g. 0.3 mm.

17. The method according to claim 13, wherein said lighting elements comprise a plurality of LEDs regularly and extensively distributed in correspondence with said pattern.

18. The method according to claim 17, wherein said pattern comprises a plurality of concentric rings, said LED being arranged in annular arrays corresponding with respective rings.

19. The method according to claim 18, wherein in each annular array said LEDs are placed at an average distance of about 15 mm between two consecutive LEDs of the same array.

20. The method according to claim 13, wherein the distance between the circuit board and the disc-shaped body is substantially constant.

21. The method according to claim 13, wherein said board is wrapped over, and supported by, a support in turn configured as a paraboloid, a cone or the like which is associated at the back of the disc-shaped body forming a gap between the support and the body.

22. The method according to claim 21, wherein said board is applied over a rear convex face of the support which provides for a distribution of through orifices for arrangement and engagement of respective LEDs.

23. The method according to claim 13, wherein said board has a circuit configured to make single LEDs or groups thereof controllable in a mutually independent manner.

24. The method according to claim 23, wherein said groups of LEDs belong to respective circular sectors of the board, to single annular arrays or to sets of adjacent arrays.

* * * * *